(12) United States Patent
Kamaguchi et al.

(10) Patent No.: US 8,747,893 B2
(45) Date of Patent: Jun. 10, 2014

(54) CAPSULE WHICH DISINTEGRATES SPECIFICALLY IN THE LARGE INTESTINE

(71) Applicant: Morishita Jintan Co., Ltd., Osaka (JP)

(72) Inventors: Ryosei Kamaguchi, Hirakata (JP); Masafumi Mizutani, Hirakata (JP)

(73) Assignee: Morishita Jintan Co., Ltd., Osaka (JP)

( * ) Notice: Subject to any disclaimer, the term of this patent is extended or adjusted under 35 U.S.C. 154(b) by 0 days.

(21) Appl. No.: 13/652,543

(22) Filed: Oct. 16, 2012

(65) Prior Publication Data

US 2013/0259933 A1    Oct. 3, 2013

(30) Foreign Application Priority Data

Mar. 30, 2012 (JP) ................................ 2012-078529

(51) Int. Cl.
    *A61K 9/48*      (2006.01)
    *A61K 9/14*      (2006.01)

(52) U.S. Cl.
    USPC ............................ 424/456; 424/451; 424/488

(58) Field of Classification Search
None
See application file for complete search history.

(56) References Cited

U.S. PATENT DOCUMENTS

| | | | |
|---|---|---|---|
| 5,283,064 A | 2/1994 | Suzuki et al. | |
| 5,364,634 A * | 11/1994 | Lew | 424/451 |
| 5,478,570 A | 12/1995 | Sunohara et al. | |
| 6,248,362 B1 | 6/2001 | Tominaga et al. | |
| 6,582,727 B2 * | 6/2003 | Tanner et al. | 424/451 |
| 6,949,258 B2 * | 9/2005 | Zhang | 424/463 |
| 6,972,132 B1 * | 12/2005 | Kudo et al. | 424/461 |
| 7,604,820 B1 * | 10/2009 | Shimono et al. | 424/468 |
| 7,670,612 B2 * | 3/2010 | Miller | 424/400 |
| 7,670,624 B2 * | 3/2010 | Tsutsumi et al. | 424/489 |
| 2003/0166508 A1 * | 9/2003 | Zhang | 514/3 |
| 2004/0022845 A1 * | 2/2004 | Zhang | 424/452 |
| 2005/0249800 A1 * | 11/2005 | Kudo et al. | 424/451 |
| 2007/0128285 A1 * | 6/2007 | Jin et al. | 424/488 |
| 2007/0269566 A1 * | 11/2007 | Curtis et al. | 426/519 |
| 2007/0292502 A1 * | 12/2007 | Chang et al. | 424/463 |
| 2008/0206316 A1 * | 8/2008 | Barrow et al. | 424/450 |
| 2009/0274791 A1 * | 11/2009 | Mattson et al. | 426/2 |
| 2010/0183713 A1 * | 7/2010 | Tsutsumi et al. | 424/459 |
| 2011/0027334 A1 * | 2/2011 | Maguire et al. | 424/423 |
| 2012/0301546 A1 * | 11/2012 | Hassan | 424/465 |

FOREIGN PATENT DOCUMENTS

| | | |
|---|---|---|
| EP | 0 454 383 | 10/1991 |
| EP | 616802 A1 * | 9/1994 |
| EP | 0 629 398 | 12/1994 |
| JP | 4-41422 | 2/1992 |
| JP | 4-225922 | 8/1992 |
| JP | 6-179618 | 6/1994 |
| JP | 7-2650 | 1/1995 |
| JP | 7-2701 | 1/1995 |
| JP | 7-10745 | 1/1995 |
| JP | 7-69867 | 3/1995 |
| JP | 10-324642 | 12/1998 |
| JP | 2001-48779 | 2/2001 |
| JP | 2011-105654 | 6/2011 |
| WO | WO 01/10467 | 2/2001 |

* cited by examiner

*Primary Examiner* — Robert A Wax
*Assistant Examiner* — Olga V Tcherkasskaya
(74) *Attorney, Agent, or Firm* — Hamre, Schumann, Mueller & Larson, P.C.

(57) ABSTRACT

The present invention is to obtain capsules which do not disintegrate in stomach and intestine after orally administrating them and which disintegrate specifically in large intestine. The present invention thus provides a capsule which disintegrates specifically in large intestine, comprising a content comprising a main agent, and a shell, covering the content, comprising a natural water-soluble polymer as a shell base material and chitosan powder dispersing in the natural water-soluble polymer.

8 Claims, 1 Drawing Sheet

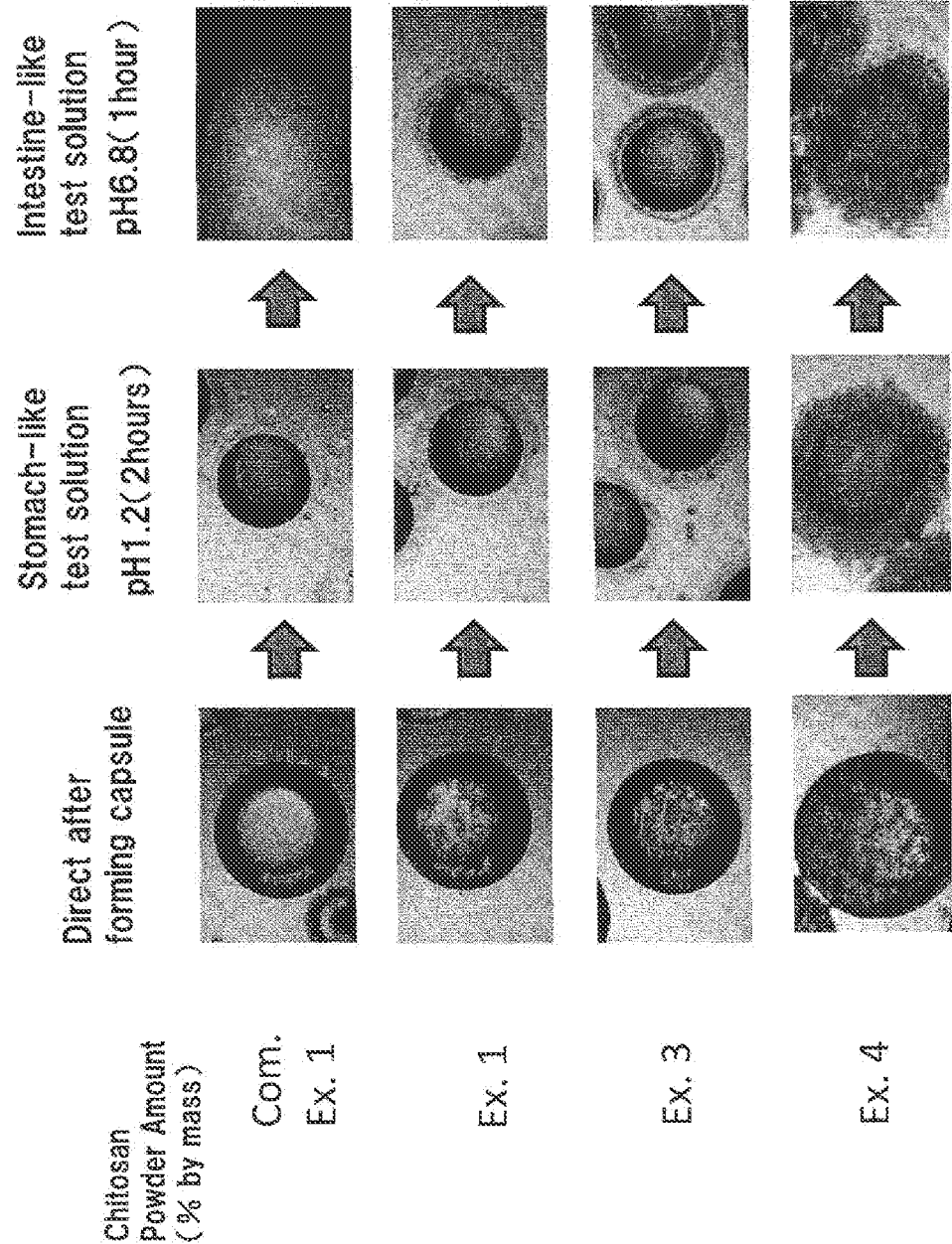

CAPSULE WHICH DISINTEGRATES SPECIFICALLY IN THE LARGE INTESTINE

FIELD OF THE INVENTION

The present invention is related to a capsule which disintegrates specifically in large intestine, in particular to a capsule which, when orally administrated, does not disintegrate in stomach and small intestine, but disintegrates in large intestine to release capsule content.

BACKGROUND OF THE INVENTION

Many main agents contained in capsules or medicines are badly affected by pH, degrading enzyme. Especially, they are orally administrated in a human passing through digestive organs in the human body and are degraded by a secretion (such as stomach acid, bile acid, pepsin, lipase and the like). It is very important for fields of medicine or functional food that such main agent is safely conveyed to an targeted portion of a human body without any degradation.

Hitherto there have been many patent applications, such as JP-A-7-2650, JP-A-7-10745, JP-A-4-41422, JP-A-4-225922, JP-A-10-324642, JP-A-2001-48779, JP-A-2011-105654, JP-A-7-2701, JP-A-6-179618, JP-A-01/10467 and JP-A-7-69867 that describe a medicine that is coated for release in the intestine.

JP-A-7-2650 and JP-A-7-10745 disclose a combination of a release-controlled medicine and an intestine-soluble coating, whereby the medicine is released after passing through a stomach in which strong acid attacks the medicine. In the technique of Patent Documents, variation of release starting times is controlled to some degree, in comparison with a medicine not having an intestine-soluble coating, but release starting times are still varied based on differences of body conditions among individuals.

JP-A-4-41422, JP-A-4-225922, JP-A-10-324642, JP-A-2001-48779 and JP-A-2011-105654 disclose that a medicine content is covered with a chitosan coating and then the chitosan coating is further covered with an intestine-soluble coating which is resistant to stomach acid. The chitosan coating is disintegrated in large intestine by action of enteric microbes or osmotic pressure to release the medicine content in large intestine. Chitosan generally does not dissolve in water or organic solvent but dissolves only in acid solution. When producing the chitosan coating, chitosan should be dissolved in acid solution and the medicine content should be covered with the chitosan acid solution. However, the chitosan coating should include acid in a small amount and can not cannot exclude acid completely. The presence of acid in the chitosan coating lowers acid resistance of the coating and may lead bad effects on the content inside the chitosan coating.

JP-A-7-2701 proposes use of water soluble chitosan having a deacetylation degree of 40 to 60%, in order to solve the problem of using acid for dissolving chitosan. The water soluble chitosan does not have enough water resistance and is not suitable for materials which specifically disintegrate in large intestine.

JP-A-6-179618 proposes a process for producing a chitosan-cured capsule, which comprises dissolving chitosan in an acid solution in which silica microparticles are dispersed, and forming it to a suitable shape by drying and solidifying, followed by treating it with alkali to remove acid residue, in order to solve the problem of using acid for dissolving chitosan. However, for actually conducting the process, additional process (e.g. rinsing the resulting capsules with water to remove excess alkali and salt as side products) is necessary together with the alkali treatment.

JP-A-01/10467 proposes that a content is covered with a water-insoluble polymer in which chitosan powder is dispersed, followed by covering it with intestine-soluble polymer (i.e. hydrophobic polymer), in order to solve the problem of using acid for dissolving chitosan. Since organic solvent is necessary for dissolving the hydrophobic polymer, the use of organic solvent necessitates safety in producing procedure and leads other problems, such as removal of organic solvent, adverse effects on the content of the capsule and enhance of production cost.

The present inventors proposed an intestine-soluble capsule of which a shell is formed from a mixture of gelatin as natural water-soluble polymer and pectin (see Patent Document 11). However, the capsule is not large intestine soluble. Capsules which disintegrate specifically in large intestine are still desired.

SUMMARY OF THE INVENTION

The present invention is to obtain capsules which do not disintegrate in stomach and small intestine after orally administrating them and which disintegrate specifically in large intestine. In addition, the capsules are safely and easily produced. The present invention is to solve the problems associated with the above-mentioned conventional capsules.

As the results of intense study for achieving the above object, the present inventors provide, by using as shell materials a natural water-soluble polymer and chitosan powder dispersed therein, a capsule which does not disintegrate in stomach and small intestine after orally administrating them and which disintegrate specifically in large intestine.

The present invention provides a capsule which disintegrates specifically in large intestine, comprising a content comprising a main agent, and a shell, covering the content, comprising a natural water-soluble polymer as a shell base material and chitosan powder dispersing in the natural water-soluble polymer.

According to the present invention, the natural water-soluble polymer preferably is a mixture of a first natural water-soluble polymer and a second natural water-soluble polymer, wherein the first natural water-soluble polymer is selected from the group consisting of gelatin, carrageenan, starch, agar, pullulan, modified starch, alginic acid, mannan and a mixture thereof, and the second natural water-soluble polymer is selected from the group consisting of pectin, gellan gum, cardlan and a mixture thereof.

Preferably, the capsule of the present invention may further comprise a plasticizer.

In addition, the chitosan powder may preferably be derived from animal or plant and is contained in an amount of 1 to 27% based on a total weight of dried shell, and the second natural water-soluble polymer is contained in an amount of 1 to 24% based on a total weight of dried shell.

Further, the above natural water-soluble polymer may preferably be a combination of gelatin as the first natural water-soluble polymer and pectin as the second water-soluble polymer.

Also, an intermediate layer(s) may preferably be present between the content and the shell.

The main agent of the present invention may preferably be selected from the group consisting of polypeptide drug, bifidobacterium, lactobacillus, lactoferrin and nattokinase.

The present invention also provides a method of producing the capsule, comprising ejecting into cooling solution a solution drop of a content containing a main agent and a shell solution comprising a natural water-soluble polymer as a shell base material and chitosan powder dispersing in the natural water-soluble polymer.

BRIEF DESCRIPTION OF THE DRAWINGS

FIG. 1 is photomicrographs of capsules showing the results of disintegration test of capsules according to the disintegration test in the Japanese Pharmacopoeia Twelfth Edition.

DETAILED DESCRIPTION OF THE PREFERRED EMBODIMENTS

The present invention is directed to a capsule which comprises a content comprising a main agent, and a shell, covering the content, comprising a natural water-soluble polymer as a shell base material and chitosan powder dispersing in the natural water-soluble polymer.

The natural water-soluble polymer used for the shell material of the capsule of the present invention can be a combination of a first water-soluble polymer which gives mechanical strength, shell-forming ability and adhesion, and a second water-soluble polymer which gives acid resistance against stomach acid. The first water-soluble polymer includes gelatin, carrageenan, starch, agar, pullulan, modified starch, alginic acid, mannan and a mixture thereof. The second water-soluble polymer includes pectin, gellan gum, cardlan and a mixture thereof.

The first water-soluble polymer may be present in an amount of 1 to 98% preferably 2 to 85%, more preferably 3 to 70%, based on a total weight of shell after drying. Amounts of less than 1% based on a total weight of dried shell lead to a lower strength of resulting capsules and those of more than 98% based on a total weight of dried shell cannot give acid resistance and disintegrating properties in the large intestine.

The second water-soluble polymer may be present in an amount of 1 to 24%, preferably 2 to 18%, more preferably 3 to 6%, based on a total weight of dried shell. Amounts of less than 1% based on a total weight of dried shell do not give enough acid resistance and those more than 24% based on a total weight of dried shell increase viscosity of shell solution and make it difficult to produce capsules.

Chitosan can be obtained by deacetylating chitin. Deacetylation can be conducted by heating in concentrated alkali. The chitin is a polysaccharide in which N-acetyl-D-glucosamine is linearly bonded with β-1,4-bond, and chitin is contained in shell of crabs or shrimps, outerlayer of insects, skeletal structure of cuttlefishes, cell wall of fungus, such as mushrooms. The chitosan employed in the present invention can be derived either from animals or plants.

The chitosan powder used for the capsule of the present invention has a particle size of from 90% or more passing through a sieve having an opening of 22 μm (580 mesh) to 90% or more passing through a sieve having an opening of 355 μm (42 mesh), preferably from 90% or more passing through a sieve having an opening of 45 μm (330 mesh) to 90% or more passing through a sieve having an opening of 250 μm (60 mesh), more preferably from 90% or more passing through a sieve having an opening of 75 μm (200 mesh) to 90% or more passing through a sieve having an opening of 180 μm (83 mesh). When the chitosan powder is smaller than the lower limit, chitosan makes natural water-soluble polymer solution high viscosity, when it is dispersed, and makes it difficult to form capsules. When the chitosan powder is larger than the upper limit, it is difficult to uniformly disperse the chitosan in a shell solution and to form capsules. The larger chitosan does not give enough disintegrating properties in large intestine.

The chitosan powder may be present in an amount of 1 to 27%, preferably 3 to 18%, more preferably 6 to 12%, based on a total amount of dried shell. Amounts of less than 1% do not show disintegrating properties in large intestine and those of more than 27% do not form capsule.

The capsule shell may contain a plasticizer to have flexibility in dried conditions. Examples of the plasticizer are glycerol, sorbitol and the like. The plasticizer may be present in the capsule shell in an amount of 1 to 50%, preferably 5 to 40%, more preferably 15 to 30%, based on a total weight of dried shell. When an amount is less than 1% based on a total weight of dried shell, the capsule shell is not resistant against vacuum drying and does not show enough flexibility after the shell is dried, to result in cracking of shell. When it is more than 50% based on a total weight of dried shell, the capsule shell is too soft and would be adhesive or would melt at an elevated temperature.

The shell of the capsule of the present invention may preferably contain an additive, such as organic acid, inorganic acid, pH adjuster, a compound having divalent ion or a mixture thereof, in order to attain large-intestine disintegrating properties for persons of achlorhydria or hypochlorhydria in which a concentration of hydrochloric acid in digestive juices in stomach is low. In case of organic acid, the capsule surface may be coated with organic acid or may be immersed in a solution of the above mentioned additives.

The capsule of the present invention has a shell thickness of 10 to 600 μm, preferably 30 to 400 μm, more preferably 40 to 250 μm after drying. Shell is thicknesses of less than 10 μm lower shell strength and those of more than 600 μm decrease an amount of content and do not give enough disintegration.

The main agent of the capsule content of the present invention is one which is preferred to be absorbed in large intestine and is degraded, decomposed or activity-decreased by change of pH or by secretions between large intestine and mouth, such as stomach acid, bile acid, protease, pepsin, lipase and like. The main agent can be a peptide drug or a therapeutic drug for ulcerative colitis, which is preferably absorbed in large intestine. The main agent can also be a substance which is degraded by stomach acid or enzyme, such as bifidobacterium, lactobacillus, protein (e.g. lactoferrin) and nattokinase.

The content of the capsule of the present invention is preferably a suspension of the main agent in a hydrophobic material which is not flowable at ambient temperature. The reason why the main agent is suspended in hydrophobic material is that the content is not badly affected by a large amount of water which is present in a production process of the capsules. Examples of the hydrophobic material are edible hydrogenated oil, sucrose fatty acid ester (SAIB), glycerol fatty acid ester, a mixture thereof or the like. Preferred hydrophobic material is hydrogenated coconut oil (WITOCAN-H, WITOCAN-42/44; Huels Company).

The suspension of the main agent with the hydrophobic material is encapsulated with the shell which is specifically disintegrated in large intestine. A process for encapsulating is not limited, but a dripping method which comprises ejecting into a solidifying solution a solution drop of a content containing a main agent and a shell solution containing comprising a natural water-soluble polymer as a shell base material and chitosan powder dispersing in the natural water-soluble polymer. The dropping method usually uses a double coaxial nozzle or a triple coaxial nozzle (see JR-A-49-059789, JP-A-51-008176 and JP-A-60-172343). The encapsulation may also be conducted by covering the content with two half-shells which are formed from the shell solution of the present invention.

When the triple coaxial nozzle is used for producing the capsule of the present invention, the content is poured out from an innermost nozzle and the shell solution is poured out from the outermost nozzle, and hydrogenated oil is poured out from the intermediate nozzle. The resulting capsule has three layered structure and the intermediate layer of hydrogenated oil protects the innermost layer of the content. The capsule of the present invention may have four-layered or more layered structure, for which a quadruple coaxial nozzle or more fold coaxial nozzle is used for producing the capsule.

The resulting capsules are dried by air at a temperature of 5 to 30° C. for 2 to 12 hours. The capsules may be subjected to vacuum drying or vacuum-freeze drying after air drying. The vacuum drying can be conducted at 0.5 to 0.002 MPa and the vacuum-freeze drying can be conducted at a temperature of less than −20° C. Time period for the vacuum (freeze) drying is not limited, but can generally be conducted for 5 to 60 hours, preferably 24 to 48 hours. Periods of less than 5 hours dry the capsules insufficiently and water present in is the shell badly affects on inside the capsule.

A size of the capsule of the present invention is not limited, but can generally be within the range of 0.3 to 10 mm, preferably 1 to 8 mm. Capsule sizes of less than 0.3 mm are too small to cover sufficient amount of the content and those of more than 0.8 mm are difficult to swallow down.

The capsule of the present invention disintegrates specifically in large intestine, but it does not have a simple structure such as an outermost layer of the capsule disintegrates in order as starting from mouth to reaching to large intestine through stomach and small intestine. In the capsule of the present invention, the shell material is composed of a composite matrix of a gel of the first natural water-soluble polymer (such as gelatin, carrageenan and starch) which imparts excellent mechanical strength, film-forming properties and adhesion to capsules, and a gel of the second natural water-soluble polymer (such as pectine) which imparts acid resistance especially against stomach acid to capsules, in which chitosan powder is dispersed.

First of all, as pH is very low in stomach having stomach acid, the first natural water-soluble polymer is partially degraded by stomach acid because the first polymer is not resistant to acid, but the second natural water-soluble polymer which has acid resistance protects the content in combination with an intermediate layer of protection if any. Chitosan which is dispersed in the natural water-soluble polymer is changed by acid solution to chitosan sol (solution), but is present within matrix of acid resistance shell and does not flow out to outside of the capsule. The capsules reach to small intestine and pH enhances to disintegrate the acid resistant shell while chitosan sols, which are dispersed in the acid resistant shell, are gelled to form chitosan film. The chitosan film surely protects the content at this stage in combination with an intermediate layer if any. When the capsules reach to large intestine, the chitosan film is attacked by organic acid and enzyme (e.g. lizoenzyme) (see JP-A-06-179681), which are produced by anaerobic microorganisms present in large intestine, to discompose, and the intermediate layer is also degraded to pour out the content of the capsules. This is evidenced by FIG. 1 which shows photographs of capsules after disintegration test of capsule according to the 12th edition of Japanese pharmacopoeia. In FIG. 1, the capsules of the present invention do not disintegrate both after immersing for 2 hours in pH 1.2 solution like inside stomach and after immersing for 2 hours in pH 6.8 solution like inside small intestine.

The capsules according to the present invention, after orally administrating, protect the content in stomach by shell film of the second natural water-soluble polymer which is resistant to stomach acid. The capsules reach to small intestine at which pH is elevated, and the acid resistant film of the second natural water-soluble polymer is disintegrated, while chitosan sols dispersed in the natural water-soluble polymer are gelled to form chitosan shell. The chitosan shell then protects the content of the capsules. The chitosan shell is then disintegrated by organic acid and enzyme (e.g. lizoenzyme) which are produced by anaerobic microorganisms present in large intestine, to release the content of the capsules. The capsules of the present invention have excellent is properties that a protective shell layer suitable for each digestive organ is continuously formed in a human body. Conventional capsules containing chitosan necessitate complicated treatments, such as neutralizing treatment with alkali and rinse and removal treatment of excess alkali (see JP-A-06-179618 etc.), but the capsules of the present invention do not need such treatment process at all.

EXAMPLES

The present invention will be explained in detail by examples which, however, are not construed as limiting the present invention.

Example 1

(i) Production of Capsules (a) Content solution: Commercially available bacteria powder of bifidobacterium longum (number of organisms being $1.5 \times 10^{11}$ number/g: obtained by freeze-drying a mixture of bifidobacterium longum organisms with a protective agent) was dispersed in hydrogenated dl at 34° C. with oligosaccharide.

(b) Shell solution: A shell solution was obtained by mixing ingredients as shown in Table 1.

A triple coaxial nozzle was prepared, in which the content solution (a) was put in an innermost nozzle, a solution of a hydrogenated oil having a melting point of 43° C. was put in an intermediate nozzle and the shell solution was put in the outermost nozzle. The three solution jet was dropped into an oil solution which was cooled and flowed, to form seamless capsules having three-structure, which have an average diameter of 1.8 mm.

The seamless capsules were air-dried at 20° C. for 6 hours and then vacuum-dried at a vacuum degree 0.4 MPa for 24 hours until the capsules had a water activity (Aw) value of 0.1 or less. Aw value used herein means an index of water which is directly contributed to chemical reaction, grow of microorganisms and the like, which is determined by a water activity measuring instrument Hygro Lab 2 available from Rotronic AG; Switzerland. Aw value is not an actual water content of a sample and can be considered to be freedom degree of water in the sample, Disintegration Test (Japanese Pharmacopoeia, Twelfth Edition)

The capsules were put in a disintegration tester NT-60H available from Toyama Sangyou Co., Ltd. and immersed for 2 hours in a stomach-like test solution (a) as follow, followed by immersing for 1 hour in an intestine-like test solution (b) as follow.

(a) Stomach-like test solution: pH 1.2
(b) Intestine-like test solution: pH 6.8

The capsules after immersing in the test solution (a) were observed by a microscope (8 times) and then those after immersing in the test solution (b) were observed by the microscope. The photographs are shown in FIG. 1.

Storage Test

The capsules obtained above were kept at 40° C. for given days to determine stability with time. A relation of period of days and number of living microorganisms is shown in Table 2.

Examples 2 to 4

Capsules were obtained as generally described in Example 1, with the exception that the shell ingredients were changed to those described in Table 1. Same tests were conducted and the results are shown in Table 2 and FIG. 1, with exception that Example 2 does not show photographs of FIG. 1 and Example 4 did not conduct the storage test of Table 2.

Comparative Example 1

Capsules were obtained as generally described in Example 1, with the exception that the shell ingredients were changed to those described in Comparative Example 1 of Table 1, in which no chitosan powder is formulated. Same tests were conducted and the results are shown in Table 2 and FIG. 1.

TABLE 1

|  | Examples | | | | Comparative |
| --- | --- | --- | --- | --- | --- |
|  | 1 | 2 | 3 | 4 | Example 1 |
| Natural water-soluble polymer | | | | | |
| Gelatin*1 | 67 g | 64 g | 61 g | — | 73 g |
| Carrageenan*2 | — | — | — | 13 g | — |
| Pullulan | — | — | — | 3 g | — |
| Starch*3 | — | — | — | 44 g | — |
| Pectin*4 | 3 g | 3 g | 3 g | 3 g | 3 g |
| Chitosan powder*5 | 6 g | 9 g | 12 g | 9 g | — |
| Glycerol*6 | 24 g | 24 g | 24 g | 25 g | 24 g |
| Gelation auxiliary*7 | — | — | — | 1 g | — |
| pH adjuster*8 | — | — | — | 2 g | — |
| Purified water | 400 mL | 400 mL | 400 mL | 400 mL | 365 mL |

*1 An acid-treated gelatin derived from pig skin (gelly strength: 240 bloom)
*2 k-Type carrageenan
*3 DE (degree of esterification) value: 16
*4 Low methoxylized (LM) pectin (DE value: 27)
*5 Chitosan derived from crabs (actylized degree of more than 80; particle size: 90% or more passing through a sieve having an opening size of 250 μm (60 mesh), according to sieve test standard JIS Z8801.
*6 Concentrated glycerol for food additive.
*7 Potassium chloride, calcium chloride.
*8 Potassium hydrogenphosphate, dipotassium hydrogenphosphate.

TABLE 2

Table 2 shows the results as number of living organisms.

|  | Examples | | | Comparative Example |
| --- | --- | --- | --- | --- |
|  | 1 | 2 | 3 | 1 |
| Starting point | $2.5 \times 10^{10}$ | $2.3 \times 10^{10}$ | $1.9 \times 10^{10}$ | $1.3 \times 10^{10}$ |
| After 2 weeks | $1.6 \times 10^{10}$ | $1.3 \times 10^{10}$ | $9.1 \times 10^{9}$ | $8.1 \times 10^{9}$ |
| After 1 month | $8.5 \times 10^{9}$ | $4.3 \times 10^{9}$ | $3.1 \times 10^{9}$ | $1.1 \times 10^{9}$ |

The capsules of the present invention keep the content in stomach and small intestine from pouring out as evidenced by the disintegration test of Japanese pharmacopoeia, the twelfth edition. Accordingly, when Bifidobacterium is encapsulated as the content of the capsules, the capsules are not disintegrated in stomach and small intestine and are disintegrated after carrying the bifidobacterium to large intestine, The capsules which do not have chitosan powder in Comparative Example 1 are disintegrated in small intestine and not all of the content is conveyed to large intestine.

As is apparent from the results of the storage test in Table 2, the formulation of chitosan powder in capsule shell does not badly affect on number of living microorganisms in storage test and keeps the capsules for a long period of time without damaging living microorganisms in the capsules.

INDUSTRIAL APPLICABILITY

The present invention provides capsules which are not disintegrated in stomach and small intestine after orally administrating and which are disintegrated specifically in large intestine, which is very useful in the field of medicines, functional food and the like.

What is claimed is:

1. A capsule for delivering a main agent to a large intestine, comprising:
   an inner layer that includes a composition comprising the main agent, and
   a shell that is an outermost layer of the capsule,
   wherein the shell comprises a natural water-soluble polymer matrix as a shell base material and a chitosan powder that is dispersed within the natural water-soluble polymer matrix,
   wherein the natural water-soluble polymer matrix comprises a first natural water-soluble polymer that is at least one selected from the group consisting of gelatin, carrageenan, starch, agar, pullulan, modified starch, alginic acid and mannan and a second natural water-soluble polymer that is at least one selected from the group consisting of pectin, gellan gum and cardlan,
   wherein the first water-soluble polymer is present in an amount of 1 to 98%, the second natural water-soluble polymer is present in an amount of 1 to 24%, and the chitosan powder is present in an amount of 1 to 27%, said amounts being based on the total weight of a dried shell.

2. The capsule according to claim 1, which further comprises a plasticizer.

3. The capsule according to claim 1, wherein the chitosan powder is derived from animal or plant.

4. The capsule according to claim 1, wherein the natural water-soluble polymer is a combination of gelatin as the first natural water-soluble polymer and pectin as the second water-soluble polymer.

5. The capsule according to claim 1, wherein at least one intermediate layer is present between the inner layer and the shell.

6. The capsule according to claim 1, wherein the main agent is at least one selected from the group consisting of polypeptide drug, bifidobacterium, lactobacillus, lactoferrin and nattokinase.

7. The capsule according to claim 6, wherein the main agent is at least one selected from the group consisting of bifidobacterium and lactobacillus.

8. The capsule according to claim 6, wherein the shell comprises
   (c) a plasticizer.

* * * * *